United States Patent
Sasaki et al.

(10) Patent No.: US 10,401,140 B2
(45) Date of Patent: Sep. 3, 2019

(54) BENDING DETECTING SYSTEM, LIGHT GUIDE BODY, TUBULAR APPARATUS, LIGHT DETECTING APPARATUS, LIGHT DETECTING METHOD, AND OPTICAL BENDING MEASURING APPARATUS

(71) Applicant: OLYMPUS CORPORATION, Tokyo (JP)

(72) Inventors: Yasuo Sasaki, Machida (JP); Eiji Yamamoto, Musashimurayama (JP); Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/701,551

(22) Filed: Sep. 12, 2017

(65) Prior Publication Data

US 2017/0370697 A1    Dec. 28, 2017

Related U.S. Application Data

(63) Continuation-in-part of application No. PCT/JP2015/057519, filed on Mar. 13, 2015.

(51) Int. Cl.
*G01B 9/02* (2006.01)
*G02B 6/02* (2006.01)
(Continued)

(52) U.S. Cl.
CPC ..... *G01B 9/02027* (2013.01); *G01B 9/02015* (2013.01); *G01B 11/18* (2013.01);
(Continued)

(58) Field of Classification Search
CPC ............ G01B 9/02015; G01B 9/02027; G01B 9/02049; G01D 5/353; G01D 5/35303;
(Continued)

(56) References Cited

U.S. PATENT DOCUMENTS

| 6,275,628 B1 * | 8/2001 | Jones | G02B 6/02057 385/29 |
| 2004/0083808 A1 * | 5/2004 | Rambow | G01B 11/18 73/250 |

(Continued)

FOREIGN PATENT DOCUMENTS

| JP | H02-19730 A | 1/1990 |
| JP | 2010-104427 A | 5/2010 |
| JP | 2013-036925 A | 2/2013 |

OTHER PUBLICATIONS

International Search Report dated Jun. 9, 2015 issued in PCT/JP2015/057519.

(Continued)

*Primary Examiner* — Jonathan M Hansen
(74) *Attorney, Agent, or Firm* — Scully, Scott, Murphy & Presser, P.C.

(57) ABSTRACT

A bending detecting system includes a light guide, a first grating and a light detector. The light guide has elongated shape and is configured to guide an incident light in a propagating direction. The light guide includes a core and a cladding disposed around the core. The first grating is disposed in a boundary area, the boundary area including an outer surface of the core, and an adjacent area that is adjacent to the outer surface. The first grating includes a first periodic structure along the propagating direction with a first pitch, and is configured to generate a first diffracted light from the incident light. The light detector is configured to detect the first diffracted light from the first grating, and detect a bending of the light guide based upon an optical feature amount of the first diffracted light.

23 Claims, 11 Drawing Sheets

(51) Int. Cl.
*G01B 11/16* (2006.01)
*G02B 6/14* (2006.01)

(52) U.S. Cl.
CPC ....... *G02B 6/0208* (2013.01); *G02B 6/02057* (2013.01); *G02B 6/14* (2013.01)

(58) Field of Classification Search
CPC ........... G01D 5/35316; G01D 5/35354; G01D 5/3537; G01D 5/35374; G01D 5/35383
See application file for complete search history.

(56) References Cited

U.S. PATENT DOCUMENTS

| | | | |
|---|---|---|---|
| 2007/0297712 A1 | 12/2007 | Meneghini et al. | |
| 2008/0085080 A1* | 4/2008 | Dimmick ........... | G01K 11/3206 385/37 |
| 2009/0185772 A1* | 7/2009 | Xia ...................... | A61B 5/0059 385/13 |
| 2009/0263072 A1* | 10/2009 | Albert ................... | G01B 11/18 385/13 |

OTHER PUBLICATIONS

Meltz, G. et al., "Formation of Bragg gratings in optical fibers by a transverse holographic method", Optics Letters (Aug. 1, 1989), vol. 14, No. 15, pp. 823-825.
Born et al., Principles of Optics, vol. 5, 13.5, Equation (85), with English translation.
English translation of International Preliminary Report on Patentability dated Sep. 28, 2017 together with the Written Opinion received in related International Application No. PCT/JP2015/057519.
Japanese Office Action dated Jul. 3, 2018 in Japanese Patent Application No. 2017-505776.

* cited by examiner

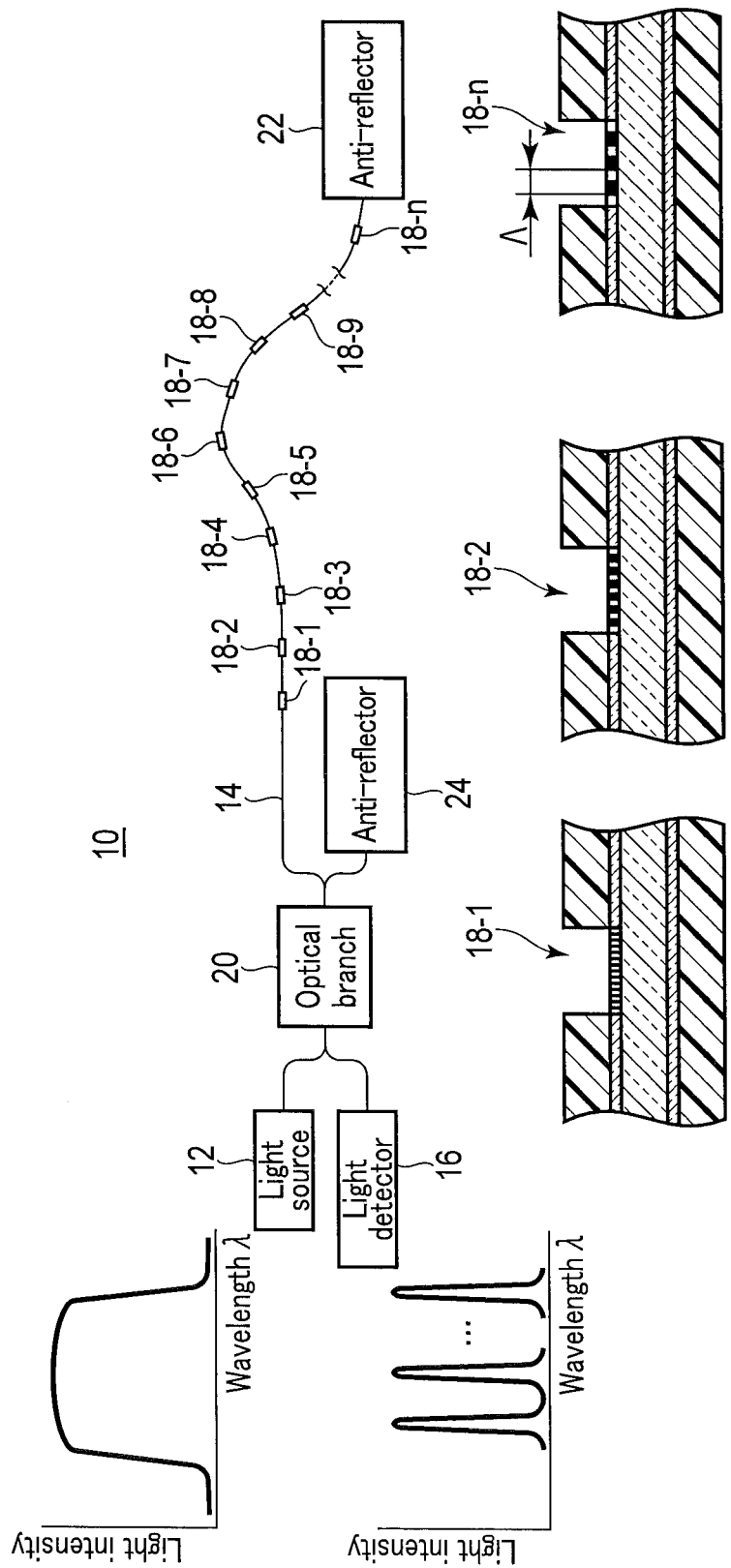
F I G. 1

F I G. 6A
F I G. 6B
F I G. 6C
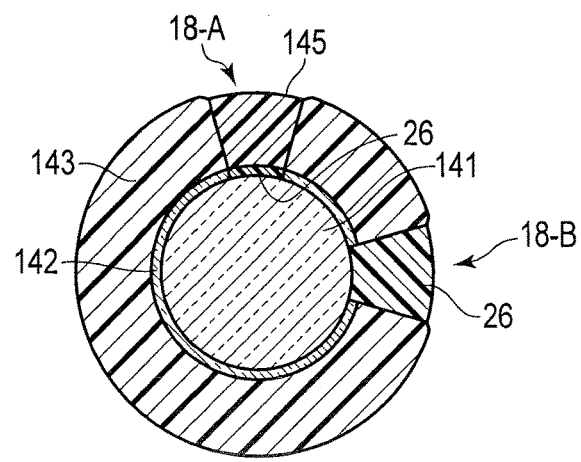
F I G. 7A

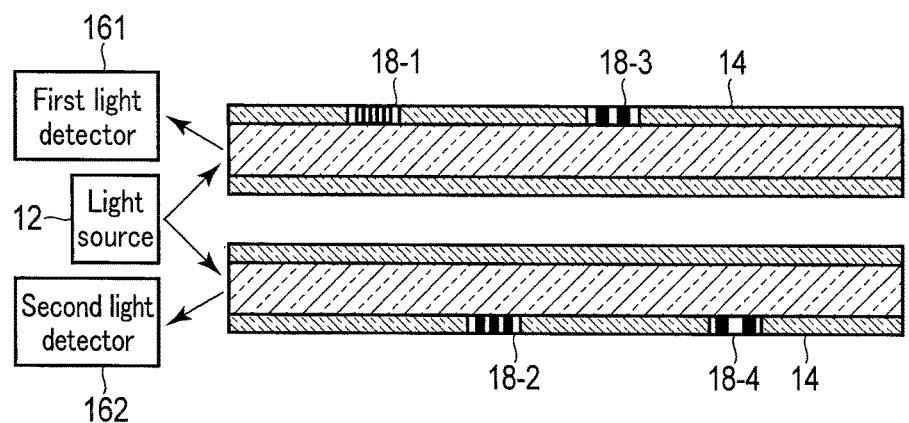
F I G. 15
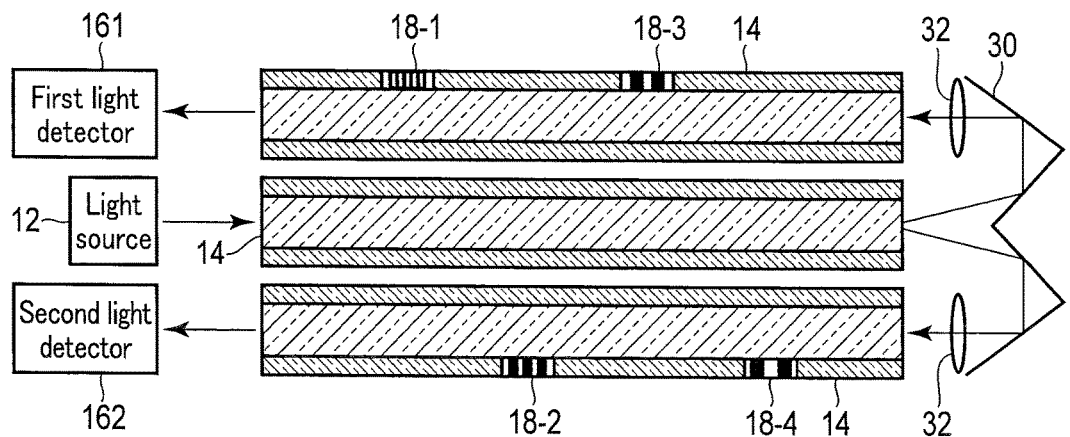
F I G. 16

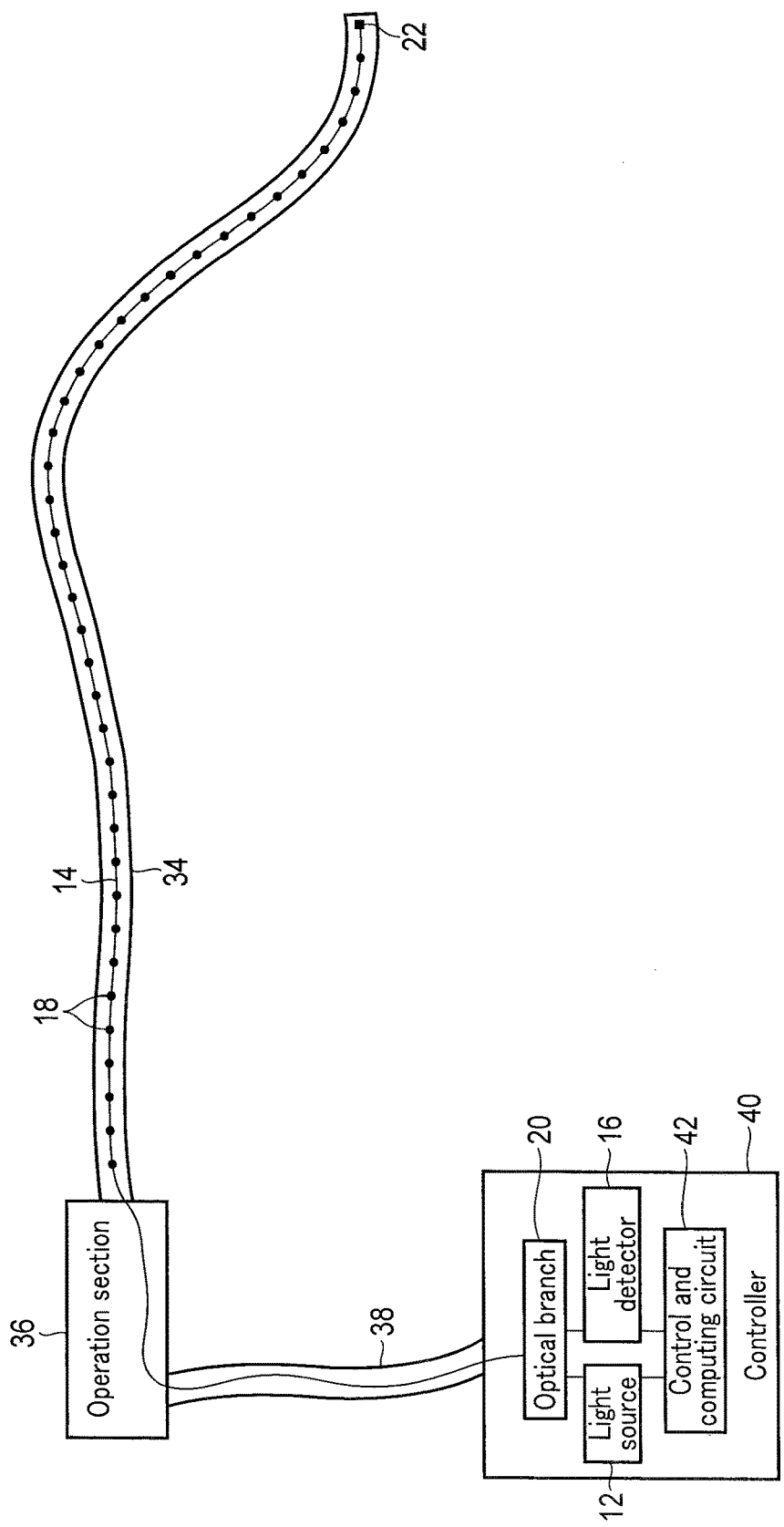
F I G. 17

BENDING DETECTING SYSTEM, LIGHT GUIDE BODY, TUBULAR APPARATUS, LIGHT DETECTING APPARATUS, LIGHT DETECTING METHOD, AND OPTICAL BENDING MEASURING APPARATUS

CROSS-REFERENCE TO RELATED APPLICATIONS

This application is a Continuation-in-part Application of PCT Application No. PCT/JP2015/057519, filed Mar. 13, 2015, the entire contents of which are incorporated herein by reference.

BACKGROUND OF THE INVENTION

1. Field of the Invention

The present invention relates to a bending detecting system, a light guide body, a tubular apparatus, a light detecting apparatus, a light detecting method, and an optical bending measuring apparatus.

2. Description of the Related Art

"Formation of Bragg gratings in optical fibers by a transverse holographic method", written by G. Meltz et al., (US), Vol. 14, No. 15, Optics Letters, 1989, Aug. 1, p. 823-825 describes that an optical fiber can be used in strain sensing and temperature sensing by the formation of a grating in a core of the optical fiber.

BRIEF SUMMARY OF THE INVENTION

According to a first aspect of the present invention, there is provided a bending detecting system comprising: a light guide, having elongated shape, configured to guide an incident light in a propagating direction, wherein the light guide comprises: a core; and a cladding disposed around the core; a first grating disposed in a boundary area, the boundary area comprising: an outer surface of the core; and an adjacent area that is adjacent to the outer surface, wherein the first grating comprises a first periodic structure along the propagating direction with a first pitch, and wherein the first grating is configured to generate a first diffracted light from the incident light; and a light detector configured to: detect the first diffracted light from the first grating; and detect a bending of the light guide based upon an optical feature amount of the first diffracted light.

According to a second aspect of the present invention, there is provided a light guide body comprising: a light guide, having elongated shape, configured to guide an incident light in a propagating direction, wherein the light guide comprises: a core; and a cladding disposed around the core; a first grating disposed in a boundary area of a boundary between the core and the cladding, wherein the first grating comprises a first periodic structure along the propagating direction with a first pitch, and wherein the first grating is configured to generate an first diffracted light form the incident light; and a second grating, disposed in the boundary area of the boundary, wherein the second grating comprises a second periodic structure along the propagating direction with a second pitch, and wherein the second grating is configured to generate a second diffracted light from the incident light, wherein the second grating is configured to be disposed in a position different from a position of the first grating about at least one of a propagating direction and a predetermined axis direction of the light guide, the predetermined axis direction being perpendicular to the propagating direction.

According to a third aspect of the present invention, there is provided a tubular apparatus comprising the light guide body according to the second aspect.

According to a fourth aspect of the present invention, there is provided a light detecting apparatus for detecting bending of a light guide, the light detecting apparatus comprising: a light detector configured to: detect a first diffracted light from the light guide, the first diffracted light being generated from an incident light emitted into the light guide; and detect a bending of the light guide based upon an optical feature amount of the first diffracted light.

According to a fifth aspect of the present invention, there is provided a light detecting method comprising: detecting a first diffracted light from a light guide; and determining the light guide is bending based upon an optical feature amount of the first diffracted light.

According to a sixth aspect of the present invention, there is provided an optical bending measuring apparatus for measuring bending of a light guide, the optical apparatus comprising: a light source which supplies measurement light; a light guide which has a core and a cladding and which transmits the measurement light in a longitudinal axis direction thereof; sensing parts provided in positions different in the longitudinal axis direction of the light guide and each having a grating, the grating being provided in contact with the core or provided in parts of the cladding, and the grating generating diffracted lights from the measurement light being traveled in the core; a light detector which detects lights including the diffracted lights output from the light guide; and a processer which separates the diffracted lights at respective wavelengths from the lights, and independently measures bending amounts of the positions of the light guide on the basis of an intensity change of the separated diffracted lights.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a schematic configuration of an optical bending measuring apparatus according to a first embodiment of the present invention;

FIG. 6A is a diagram showing an example of a grating;

FIG. 6B is a diagram showing another example of a grating;

FIG. 6C is a diagram showing yet another example of a grating;

FIG. 7A is a sectional view showing yet another example of the configuration of the sensing part in the light guide body;

FIG. 15 is a diagram showing a schematic configuration of an optical bending measuring apparatus according to a fourth embodiment of the present invention;

FIG. 16 is a diagram showing a schematic configuration of a modification of the optical bending measuring apparatus according to the fourth embodiment; and FIG. 17 is a block diagram showing a schematic configuration of an endoscope as a tubular apparatus according to a fifth embodiment of the present invention equipped with the optical bending measuring apparatus according to the first embodiment.

DETAILED DESCRIPTION OF THE INVENTION

Figure 2:
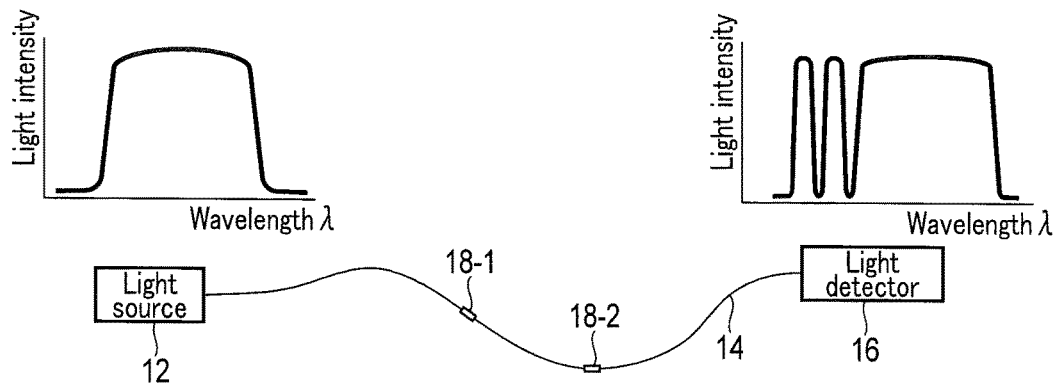
FIG. 2 is a block diagram showing a schematic configuration of a modification of the optical bending measuring apparatus according to the first embodiment.

Hereinafter, embodiments of the present invention will be described with reference to the drawings.

First Embodiment

As shown in FIG. 1, an optical bending measuring apparatus 10 according to the first embodiment of the present invention includes a light source 12, a light guide 14, a light detector 16, sensing parts 18 (in the example in FIG. 1, n sensing parts 18-1, 18-2, . . . , 18-9, . . . , and 18-n), an optical branch 20, and anti-reflectors 22 and 24.

Here, the light source 12 is a light source unit which supplies measurement light. The light guide 14 is a flexible light transmitter which has a core and a cladding covering the circumference of the core and lower in refractive index than the core and which transmits the measurement light from the light source 12 in its longitudinal axis direction. The light detector 16 is a light detecting unit which detects light output from the light guide 14. The sensing parts 18-1, 18-2, . . . , and 18-n are provided in parts different in the longitudinal axis direction of the light guide 14 and have a grating, respectively. Each grating is provided adjacent to the core of the light guide 14 or provided in parts of the cladding of the light guide 14, and is set to mutually reinforce lights of a specific wavelength traveling in a predetermined direction. The optical branch 20 optically connects the light source 12 and the light detector 16 to one end of the light guide 14, and thereby allows the measurement light from the light source 12 to enter one end of the light guide 14, and also allows the light from one end of the light guide 14 to enter the light detector 16. The anti-reflector 22 inhibits the reflection of the measurement light so that the measurement light may not be reflected at the other end of the light guide 14 and may be least transmitted in the light guide 14 in the opposite direction. The anti-reflector 24 inhibits the reflection of the measurement light to minimize the amount of the measurement light that is reflected in the optical branch 20 and thus enters the light detector 16. A light guide body according to the present embodiment includes the light guide 14 and the gratings of the sensing parts 18.

Although the light source 12 and the light detector 16 are on the same side of the light guide 14 in the configuration in FIG. 1, the light source 12 and the light detector 16 may be on different sides of the light guide 14. In this case, as shown in FIG. 2, the optical bending measuring apparatus 10 according to the present embodiment includes the light source 12, the light guide 14, the light detector 16, and the sensing parts 18 (in the example in FIG. 2, two sensing parts 18-1 and 18-2).

In the present embodiment, the light detector 16 separates the lights which are subjected to light modulation of the specific wavelength caused in the gratings of the sensing parts 18 into lights for respective wavelengths, and independently measures bending amounts of the parts of the light guide 14 in the specific direction on the basis of the intensity change of the separated light for each wavelength. Although the light detector 16 detects lights output from the light guide 14, separates into lights for respective wavelengths and independently measures the bending amounts, only the light detection may be performed in the light detector 16 and the separation into lights for respective wavelengths and the independently measuring of the bending amounts are may be performed by a processor connected to the light guide.

The configuration of each part is described in detail below.

The light source 12 supplies, as the measurement light, white light having a substantially uniform light spectrum in, for example, a wide range of wavelength bands shown in FIG. 1.

Figure 3A:
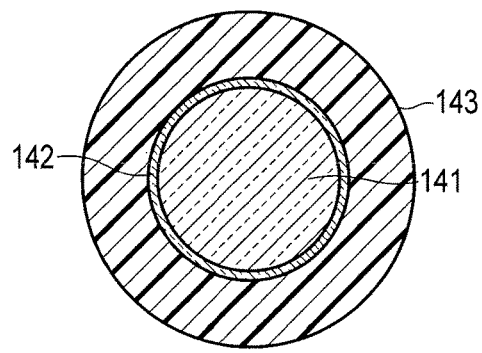
FIG. 3A is a sectional view showing the shape of an example of a light guide body.

The light guide 14 can include, for example, an optical fiber. FIG. 3A shows a sectional structure in a diametrical direction which is a direction orthogonal to the longitudinal axis direction of this optical fiber. That is, the above optical fiber includes a core 141 which is present in the center and which guides light, a cladding 142 which is provided around the core 141 and which stably confines the light in the core 141, and a jacket 143 which protects the core 141 and the cladding 142 from physical shocks and thermal shocks.

Figure 3B:
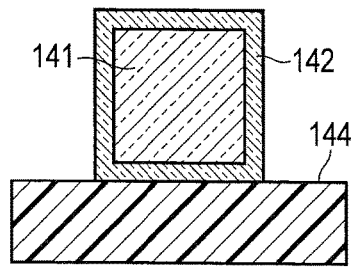
FIG. 3B is a sectional view showing the shape of another example of a light guide body.

Alternatively, the light guide 14 may include an optical waveguide. As shown in FIG. 3B, the optical waveguide is provided with, on a flexible substrate 144, the core 141 and the cladding 142 that serve equivalently to those of the above optical fiber.

The case where the light guide 14 includes the above optical fiber is taken as an example to describe the configuration of the optical bending measuring apparatus 10 below in more detail. In the present embodiment, this optical fiber is a single-mode optical fiber.

Figure 4A:
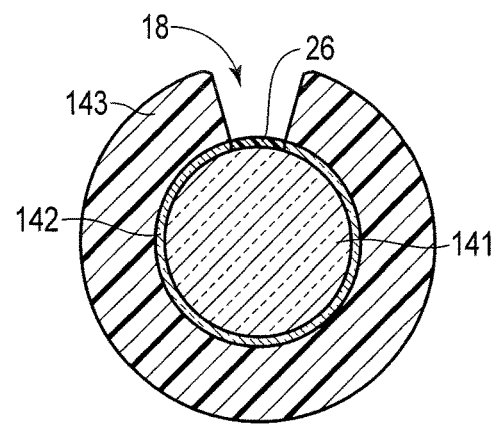
FIG. 4A is a sectional view showing an example of the configuration of a sensing part in the light guide body in FIG. 3A.
Figure 4B:
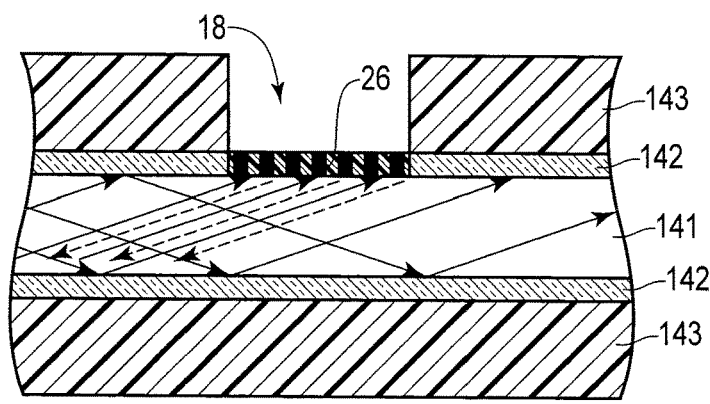
FIG. 4B is a sectional view of a sensing part portion of the light guide body in FIG. 4A, taken along the longitudinal axis direction of the light guide body.

The optical fiber which is the light guide 14 of the optical bending measuring apparatus 10 has the sensing parts 18, each sensing part 18 being provided in each part in which a bending amount is to be measured, as shown in FIG. 4A and FIG. 4B. That is, the sensing part 18 is a part in which the jacket 143 and the cladding 142 are removed to expose a part of the core 141 at a desired position in the longitudinal axis direction of the optical fiber, and a grating 26 that is an optical characteristics changing member is holographically made of a photopolymer in the exposed part of the core 141. The jacket 143 and the cladding 142 are removed by use of laser processing or photographic and etching processes. In this instance, microscopically damaging of the core 141 leads to light leakage, to loss of light to be guided, and to weakness against bending, so that processing that least damages the core 141 is desirable.

Figure 5A:
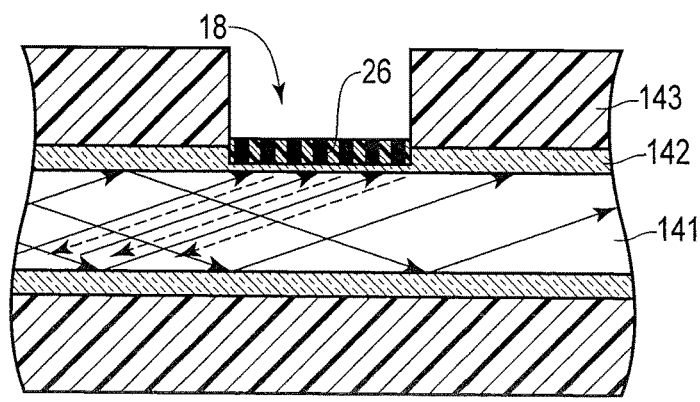
FIG. 5A is a sectional view taken along the longitudinal axis direction of the light guide body, showing another example of the configuration of the sensing part in the light guide body.
Figure 5B:
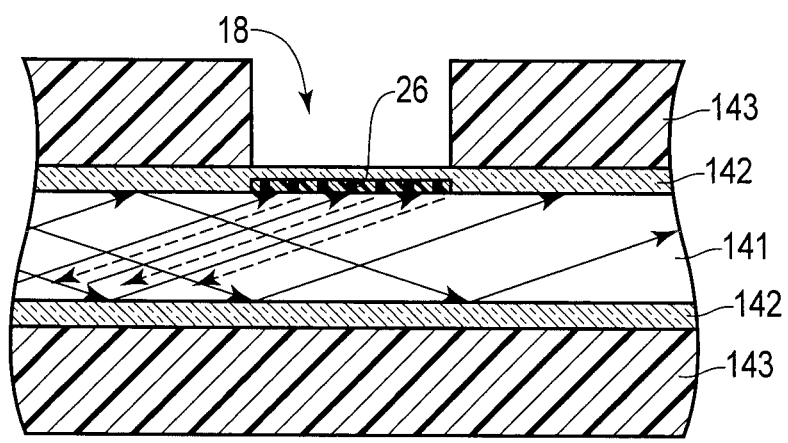
FIG. 5B is a sectional view taken along the longitudinal axis direction of the light guide body, showing yet another example of the configuration of the sensing part in the light guide body.

As above, the sensing part 18 is formed so that the grating 26 contacts the core 141. The grating 26 may be formed in a part of the cladding 142 as shown in FIG. 5A without contacting the core 141. Moreover, the grating 26 may be formed on the outer peripheral surface of the core 141 as shown in FIG. 5B. That is, the grating 26 is formed in a boundary area between the core 141 and the cladding 142. Here, the boundary area includes the outer surface of the core and an adjacent area which is adjacent to the outer surface of the core.

Furthermore, in FIG. 5A, for the light which has entered the cladding 142 from the core 141, the grating 26 should be disposed in a neighboring area located within one wavelength of incident light or less from the outer surface of the core so that the intensity of light necessary for diffraction reaches the grating 26.

The grating 26 propagates lights so that the lights cause diffraction phenomena when propagating in the grating 26 or when reflected on the surface thereof, to mutually reinforce lights of a specific wavelength traveling in predetermined direction different from the direction to enter the grating 26. In FIG. 4B, the measurement lights are indicated by solid arrows, and the lights of the specific wavelength that are made to travel in the predetermined direction by the grating 26 are indicated by broken arrows.

The specific wavelength can be set by the structure of the grating 26 as will be described in detail later. For example, as shown in FIG. 6A to FIG. 6C, the grating 26 can include a periodic structure, and the specific wavelength can be set by this period (pitch length $\Lambda$).

In the present embodiment, the refractive index of the grating 26 is lower than the refractive index of the core 141.

Each sensing part may have the grating 26 that is bare as shown in FIG. 4A, FIG. 4B, and FIG. 5A. However, as in a sensing part 18-A shown in FIG. 7A, the part in which the jacket 143 and the cladding 142 are removed on the grating 26 may be filled with a jacket-like member as a sensing part protector 145 to recover the original shape of the optical fiber. Alternatively, as in a sensing part 18-B shown in FIG. 7A, the grating 26 may be formed to fill the part in which the jacket 143 and the cladding 142 are removed to recover the original shape of the optical fiber.

In FIG. 1 and FIG. 2, more than one sensing part 18 are provided along the longitudinal axis of the optical fiber which is the light guide 14. The sensing parts 18 may be not only arranged as above, but may be also arranged so that for one sensing part 18 (the sensing part 18-A), the other sensing part 18 (the sensing part 18-B) having a different specific wavelength may be provided at the same place on the longitudinal axis of the optical fiber in an orthogonal direction or in a diametrically axially different direction, as shown in FIG. 7A. In this structure, it is possible to not only measure the bending amounts in the parts corresponding to the sensing parts 18-A and 18-B but also measure the direction of bending.

Figure 7B:
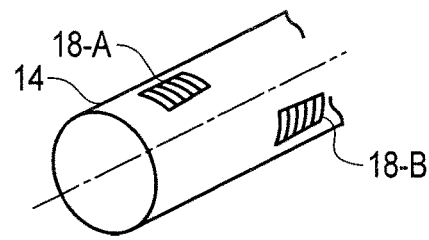
FIG. 7B is a diagram illustrating a modification of a sensing part portion of the light guide body in FIG. 7A.

When the sensing parts 18-A and 18-B are disposed at the same place on the longitudinal axis of the optical fiber, the rigidity in this part deteriorates, and this part is weak against bending. Meanwhile, the bending amounts measured by the light detector 16 on the basis of the intensity change of the lights are not only related to the parts in which the sensing parts 18 of the optical fiber are provided but also related to parts around a measurement range of a predetermined length including the above sensing parts 18. Therefore, as shown in FIG. 7B, the sensing parts 18-A and 18-B may be disposed substantially at the same place on the longitudinal axis of the optical fiber to inhibit the deterioration of rigidity.

Figure 8:
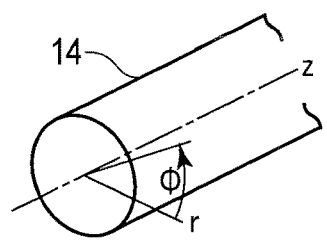
FIG. 8 is a diagram illustrating cylindrical coordinates of the light guide body.

As above, the sensing parts 18 may be provided substantially at the same place on the longitudinal axis (z-axis) of the optical fiber in directions orthogonal to each other or in directions different in $\Phi$ (cylindrical coordinates of the optical fiber which is the light guide 14 are as shown in FIG. 8). When the sensing parts 18 are produced at different positions in the z-direction and at the different positions in the $\Phi$-direction, it is possible to detect curvatures (the degrees of bending) in various directions at various positions.

The principle of the grating 26 of the sensing part 18 is described below. For convenience of explanation, the basic principle of the grating 26 in the case of a fiber bragg grating (FBG) which is an existing technique is described at the beginning.

Figure 9:
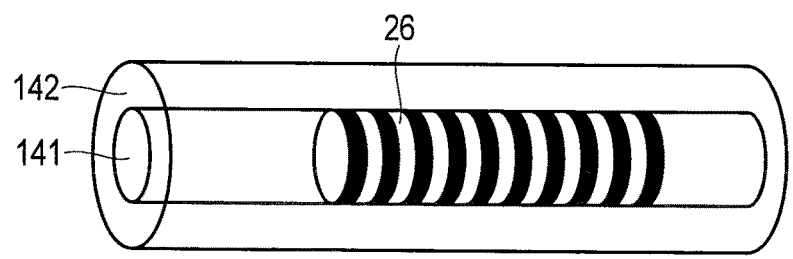
FIG. 9 is a diagram illustrating the basic principle of a grating in the case of a fiber bragg grating (FBG)

As shown in FIG. 9, the FBG has the grating 26 written in the core 141 of the single-mode fiber. When the pitch length of the grating 26 is $\Lambda$, light of a wavelength $\lambda_B = 2n\Lambda$ (in vacuum) is selectively reflected by the grating 26 ($n$ is the refractive index of the core 141).

This is as follows when considered by use of a wave number $k$ which is a reciprocal of the wavelength $\lambda$.

The relation between the wavelength λ and the wave number k is k=2π/λ. A first-order diffraction can be described below as a conservation law of a wave number vector K (the capital K represents a vector in the present description) having a magnitude k and having a direction in the traveling direction of waves.

Figure 10A:
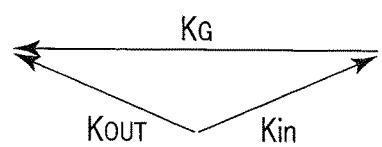
FIG. 10A is a diagram illustrating a diffraction wave in the FBG.

As shown in FIG. 10A, in the core 141, a wave of a wave number vector $K_{in}$ generates a wave of a wave number vector $K_{out}$ by a first-order diffraction of a wave number vector $K_G$ ($K_G=2\pi/\Lambda$) of the grating 26, where $K_{out}$ is $K_{out}=K_{in}+K_G$. In the single-mode fiber, the wave number vectors $K_{in}$ and $K_{out}$ in a propagation mode are substantially in the z-direction. Because the magnitude of the wave number does not change due to diffraction, $k_{in}=k_{out}$.

Figure 10B:
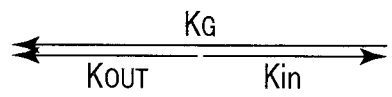
FIG. 10B is a diagram illustrating a diffraction wave in the FBG in the case of a single-mode fiber.

These two conditions are satisfied when an incoming wave number (in the core 141) $k_{in}=2\pi/(2\Lambda)$ and the wave number of the grating 26 $k_G=2\pi/\Lambda$, as shown in FIG. 10B. In this instance only, a diffraction wave which propagates in the single-mode fiber in the opposite direction can be output.

Figure 11A:
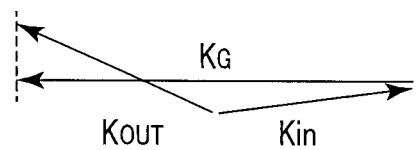
FIG. 11A is a diagram illustrating a diffraction wave in the grating of the sensing part of the optical bending measuring apparatus according to the first embodiment.

When the cladding 142 has the grating 26 as in the present embodiment as well, the light which has entered a core-cladding interface causes diffraction similar to the above diffraction, so that a first-order diffracted light of the grating 26 at this position is reflected. However, because diffraction mostly takes place at the core-cladding interface, the conservation law of the wave number is not the above conservation law $K_{out}=K_{in}+K_G$, but is the conservation law of a direction along the surface, that is, a z-component as shown in FIG. 11A. This can be written as $k_{out},z=k_{in},z+k_G$. In the single-mode fiber, the wave number vectors $K_{in}$ and $K_{out}$ in the propagation mode are substantially in the z-direction as described above, so that this is the same as the case where the grating 26 is written in the core 141 as shown in FIG. 11B.

Figure 11B:
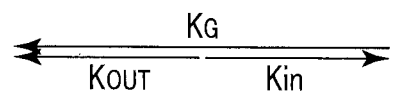
FIG. 11B is a diagram illustrating a diffraction wave in the case of the single-mode fiber.
Figure 11C:
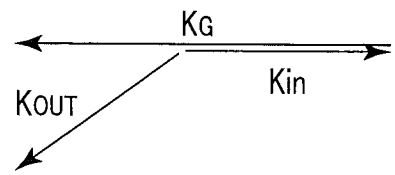
FIG. 11C is a diagram illustrating another example of a diffraction wave in the case of the single-mode fiber.

However, the conservation law is limited to the z-direction, so that when $k_{in}>k_G/2$, there is a possibility of coupling with a non-straightly traveling mode as shown in FIG. 11C. This leads to a cladding mode, which causes light loss and noise. There is no problem as long as the coefficient of coupling with the cladding mode is low, but countermeasures are needed when the coupling coefficient is high. Because this loss is caused only when $k_{in}>k_G/2$, the gratings 26 through which the light of the specific wave number vector $K_{in}$ passes before the light of the specific wave number vector $K_{in}$ reaches the grating 26 where the light is as shown in FIG. 11B, have only to satisfy $k_{in}<k_G/2$. That is, the gratings 26 are produced in the order in which the wave number $k_G$ does not increase (i.e. in the order in which the pitch length Λ of the grating 26 does not decrease) from a side close to the light source 12 to a far side.

This prevents the light of the wave number vector $K_{in}$ from causing the cladding mode before reaching the grating 26 where the light is as shown in FIG. 11B, and then causing a loss. The cladding mode that has been caused is generally attenuated at a certain distance, and therefore does not affect other gratings 26 and the light detector 16.

Thus, the specific wave number vector $K_{in}$ is present for the specific sensing part 18 of the optical fiber which is the light guide 14, and in the configuration in FIG. 1, lights of the same magnitude in opposite directions return to the light detector 16 via the optical branch 20. The sectional structures of the sensing parts 18-1, 18-2, and 18-n are shown in FIG. 1 as an example in which the sensing parts 18 (the gratings 26) are arranged in the aforementioned order in particular. The pitch length Λ of the grating 26 of the sensing part 18-1 close to the light source 12 is shorter and the pitch length Λ of the grating 26 of the sensing part which the distance from the light source 12 is longer. As shown in FIG. 1, lights of wavelengths $\lambda_1$ to $\lambda_n$ corresponding to the sensing parts 18-1 to 18-n return to the light detector 16, and the light detector 16 spectrally divides the received lights, that is, separates the received lights into lights for each wavelength to detect the intensity of the light of each wavelength.

Figure 12A:
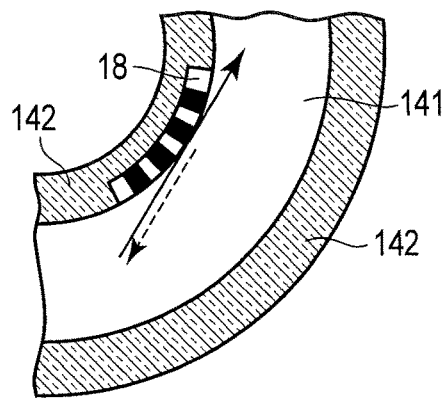
FIG. 12A is a diagram illustrating the operation principle of the optical bending measuring apparatus according to the first embodiment, and showing a case where the light guide body has bended upward in the drawing sheet.
Figure 12B:
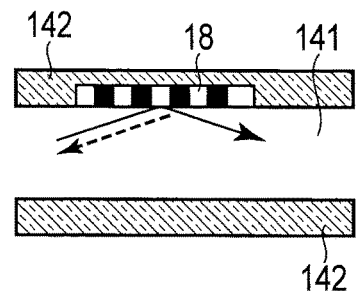
FIG. 12B is a diagram illustrating the operation principle of the optical bending measuring apparatus, and showing a case where the light guide body has not bended.
Figure 12C:
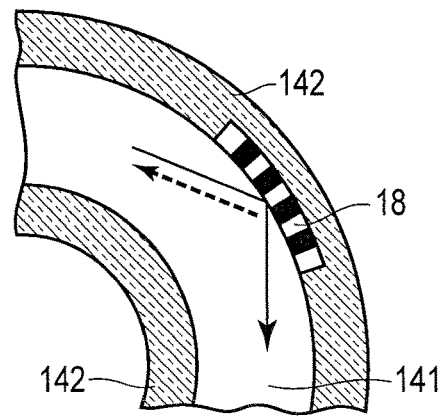
FIG. 12C is a diagram illustrating the operation principle of the optical bending measuring apparatus, and showing a case where the light guide body has bended downward in the drawing sheet.

This light intensity changes in accordance with the bending amount (curvature) in the part of the optical fiber in which the relevant sensing part 18 is provided. This is because the length of penetration of an evanescent wave into the cladding 142 changes in accordance with the angle of incidence to the core-cladding interface. As shown in FIG. 12A to FIG. 12C, light intensity is lower if the optical fiber is bent toward the sensing part 18, and light intensity is higher if the optical fiber is bent in the opposite direction (whether light intensity is high or low is represented by the thickness of the broken arrows in FIG. 12A to FIG. 12C).

Therefore, the light detector 16 can measure the curvature at a specific position of the optical fiber on the basis of the intensity change of the light dependent on the bending amount (curvature) at the place.

In addition, it is also possible to measure the curvature at a certain position of the optical fiber by use of the change of the center wavelength of light instead of the change of the intensity of wavelength-separated light. If the optical fiber is bent toward the sensing part 18 as shown in FIG. 12A, the pitch length of the grating 26 included in the sensing part 18 becomes greater than that of the grating 26 in FIG. 12B. And if the optical fiber is bent opposite to the sensing part 18 as shown in FIG. 12C, the pitch length of the grating 26 included in the sensing part 18 becomes smaller than that of the grating 26 in FIG. 12B. Since the change of the pitch length means the change of the period of the grating, the center wavelength of the first-order diffracted light generated in the grating 26 slightly changes along with the change of the pitch length. This phenomenon can be utilized to measure the curvature at a certain position of the optical fiber by use of the center wavelength of the diffracted light.

That is, the light detector 16 can measure the curvature at a certain position of the optical fiber on the basis of the change of the intensity of light or the center wavelength of light which is an optical feature amount dependent on the bending amount (curvature) at the place. Although the intensity of the diffracted light and the center wavelength of the diffracted light are shown as the optical feature amounts here, it is possible to use any optical feature amount of the diffracted light which changes in accordance with the bending amount of the optical fiber at a certain position.

As above, positions are distinguished by the wave numbers (wavelengths), so that the light source 12 and the light detector 16 that have special configurations do not need to be prepared, and the optical bending measuring apparatus 10 can be inexpensively configured.

As shown in FIG. 7A and FIG. 7B, the gratings 26 different in wave number (wavelength) from each other are formed in the Φ directions of the optical fiber so that an inexpensive apparatus can be used to measure the curvatures in predetermined different directions by the wave numbers (wavelengths). At the same time, the sensing parts 18 different in the longitudinal axis direction of the optical fiber also form the gratings 26 different in wave number (wavelength) so that the curvatures in predetermined different directions and positions can be measured by the inexpensive apparatus. Therefore, a three-dimensional shape of the optical fiber can be found by one optical fiber.

Here, in FIG. 7A and FIG. 7B, the gratings 26 which generate diffracted lights different in wave number (wavelength) from each other, that is, which are different in period (pitch length) from each other are disposed in sensing parts 18-A and 18-B, respectively. Information regarding three-dimensional positions where these gratings 26 are disposed in the optical fiber (the position of the optical fiber on the longitudinal axis and a Φ direction perpendicular to the longitudinal axis) and the period and wave number (wavelength) of each of the gratings 26 is stored in a memory. Further, as shown in FIG. 17, a processor provided in the control and computing circuit 42 reads the information stored in the memory and then refers to a change amount of the optical feature amount detected by the light detector 16, whereby a three-dimensional shape of the optical fiber can be found by one optical fiber. Moreover, the three-dimensional shape may be displayed on a display.

In the present embodiment, the cladding 142 part of the optical fiber is processed to form the grating 26. Thus, general-purpose optical fibers can be used, and the optical bending measuring apparatus 10 that uses an optical fiber can be produced inexpensively.

Such advantages are common to the other embodiments of the present invention.

When the grating 26 is not produced in the aforementioned order in which the wave number $k_G$ does not increase from the side close to the light source 12 to the far side, a light of a certain wavelength may be multiply lost by the occurrence of the cladding mode in other gratings before reflected in a specific grating 26. However, this loss also depends on the curvature for the same reason as above. Therefore, the light of this wavelength has information regarding the bending of the specific sensing parts 18 through losses and reflections that are determined by the way of arrangement. If such information is acquired for more than one wavelength, the curvature of each of the sensing parts 18 can be solved as an inverse problem.

Figure 13:
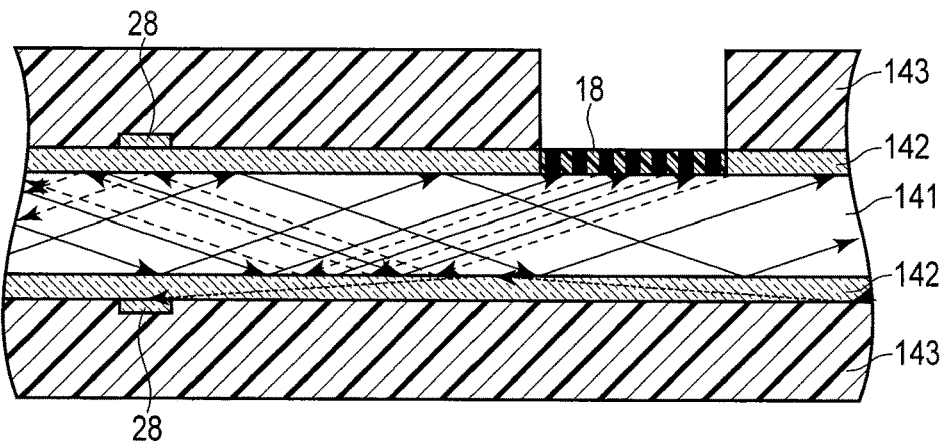
FIG. 13 is a sectional view taken along the longitudinal axis direction of the light guide body which includes a cladding mode remover.

As has been described above, the cladding mode that has been caused is generally attenuated at a certain distance. However, if reaching the light detector 16 before being fully attenuated, the cladding mode will be noise to return light that satisfies the conditions in FIG. 11B. When the noise is high to a degree that is not negligible, it is necessary to form a cladding mode remover 28 as shown in FIG. 13. This cladding mode remover 28 is, for example, a member which contacts the cladding 142, the member has a refractive index substantially equivalent to that of the cladding 142 and further includes an absorbing member, or the member attenuates the cladding mode by transmission or scattering at the interface with the external world. This cladding mode remover 28 may only be a dented surface (outer wall) of the cladding 142. The jacket 143 that is high in adhesion is also advantageous to the elimination of the cladding mode. That is, the jacket 143 can be used as the cladding mode remover 28.

The cladding mode remover 28 is suitably formed between the light detector 16 and the sensing part 18 closest thereto. Because the cladding mode may have an adverse effect such as conversion into another mode in the other sensing part 18, it is more advantageous if the cladding mode remover 28 is also formed between adjacent two sensing parts 18.

In this way, the light of the wave number particular to the grating 26 at each position only returns in the configuration in FIG. 1 even in a situation in which the cladding mode remains. Thus, reflection intensity of the light at each position can be found if the lights are spectrally divided and detected in the light detector 16 having a spectrometer.

In the configuration in FIG. 2, dips after the wave number specific to each of the positions (the sensing parts 18-1 and 18-2) are reflected is observed ($\lambda_1$ and $\lambda_2$). The depth of this dip also changes in accordance with the curvature. This configuration in FIG. 2 is also possible when coupling with the aforementioned cladding mode is not significantly great.

In any case, when the sensing part 18 has a grating structure, a signal changes due to curvature in a wavelength range limited for each of the sensing parts 18, so that the curvature at the position of each of the sensing parts 18 can be obtained.

Moreover, because the refractive index of the grating 26 is lower than the refractive index of the core 141, the main part of a waveguide mode does not penetrate the sensing part 18 except for an evanescent component. Thus, there is no unnecessary light amount loss such as conversion into the cladding mode.

If the refractive index of the grating 26 is lower than the refractive index of the cladding 142, all waveguide modes do not penetrate the sensing part 18 except for the evanescent component, so that unnecessary light amount losses are further reduced.

The grating 26 used as the sensing part 18 has a periodic structure along the traveling direction of the optical fiber as in FIG. 6A to FIG. 6C, and has a periodic structure with continuous or discontinuous refractive indexes resulting from the change of, for example, the physical properties of materials or the difference of the materials. The change may be a refractive index change of a real part or may be a refractive index change of an imaginary part. This is attributed to the following reason. The diffraction by the grating 26 is caused by the integration of periodic changes of scattering from each point of the grating 26. Regarding the scattering, scattering amplitude is represented as below in the case of Rayleigh scattering (the source of the equation: Born, Wolf, Principles of Optics, vol. 5, 13.5, Equation (85)).

$$s = i\left(\frac{2\pi a}{\lambda}\right)^3 \frac{\tilde{n}^2 - 1}{\tilde{n}^2 + 1}$$

wherein, S is complex scattering amplitude, $a$ is a particle diameter, ñ is a relative complex refractive index of a scatterer, and λ is a wavelength.

As above, the scattering can be represented not only as the Rayleigh scattering but also as the function of the complex refractive index n, and the scattering intensity can be periodically changed by both the real part and imaginary part of the refractive index.

The grating 26 is holographically produced by, for example, a photopolymer. The grating 26 is produced not only on the surface of the photopolymer but also in its inside, so that the evanescent component efficiently couples with the grating 26.

Second Embodiment

While the light guide 14 is a single-mode light guide in the first embodiment described above, the present invention is also applicable to a multi-mode light guide 14.

In the case of the multi-mode fiber as well, light intensity changes in accordance with the bending amount (curvature) in the part of the optical fiber in which the relevant sensing part 18 is provided. One reason is that the penetration length of the evanescent wave into the cladding 142 changes in accordance with the angle of incidence to the core-cladding interface as in the single-mode fiber. Another reason is that the cross-sectional distribution of lightwave density changes in accordance with the angle of incidence to the core-cladding interface.

Figure 14A:
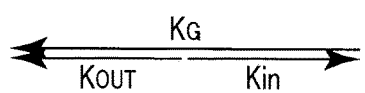
FIG. 14A is a diagram illustrating a diffraction wave in the grating in the case of a multi-mode fiber as an optical bending measuring apparatus according to a second embodiment of the present invention.
Figure 14B:
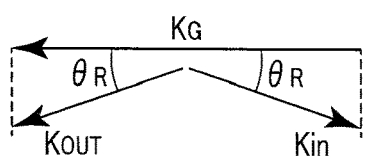
FIG. 14B is a diagram illustrating a diffraction wave in the case of the multi-mode fiber.

In the single-mode fiber, reflected light has an extremely narrow line width. In contrast, in the multi-mode fiber, a wavelength that is reflected by one grating 26 has a wide band because of the presence of many modes. For the grating 26 of the wave number vector $K_G$, reflection takes place in a wave number range from a wave number $k_{in}=k_G/2$ in the core 141 shown in FIG. 14A to a wave number $k_{in}=k_G/(2 \cos \theta_R)$ shown in FIG. 14B ($2n\Lambda \cos \theta_R < \lambda < 2n\Lambda$ for a wavelength in vacuum), wherein $\theta_R$ is a critical angle of the propagation mode in the fiber that satisfies $\sin \theta_R = NA/n$, n is the refractive index of the core 141, and NA is a numerical aperture of the fiber.

Therefore, the pitch of the gratings 26 formed in different places and directions of the optical fiber which is the light guide 14 needs to be as great as the above distance (the width of the wave number). The discriminable number decreases accordingly, but the multi-mode fiber has an advantage of being inexpensive and also has an advantage of being easily connected owing to its large core diameter when the light source 12 and the light detector 16 are separable from the optical fiber.

Figure 14C:
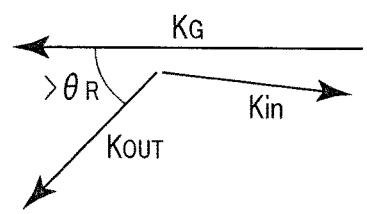
FIG. 14C is a diagram illustrating another example of a diffraction wave in the case of the multi-mode fiber.

The problem of the conversion into the cladding mode as in FIG. 14C is the same as the single-mode fiber, so that the measures similar to those in the first embodiment described above are advantageous to the order of the arrangement of the gratings 26 and the location of the cladding mode remover 28.

The grating 26 can be holographically produced by a photopolymer as in the first embodiment. A photoresist can also be used, and the grating 26 can be easily manufactured by two-beam interferometry or a phase-mask method. The structure produced with the photoresist may be replaced with some other material, or the photoresist itself may be a part of the structure.

Third Embodiment

While the refractive index of the grating 26 is lower than the refractive index of the core 141 in the first embodiment described above, the refractive index of the grating 26 may be higher than the refractive index of the core 141.

When the refractive index of the grating 26 is higher than the refractive index of the core 141, some of the light components that are reflected on the grating surface propagate in the grating and are reflected by the outer wall of the cladding 142, but are first-order-diffracted in this process and become reflection signals. Owing to advantageous effects such as the intensity of the refractive index that changes in accordance with the angle of incidence, it is possible to identify positions and curvatures as in the case where the refractive index is lower than the refractive index of the core 141.

When the refractive indexes of some portions of the grating 26 are higher than the refractive index of the core 141, the situation is somewhere between the first embodiment and the above, wherein some components of the light penetrate the cladding 142, but a first-order diffracted light is generated as described above, so that the first-order diffracted light to specify the gratings 26 is generated. Therefore, it is possible to identify positions and curvatures owing to advantageous effects similar to the above.

Fourth Embodiment

The optical bending measuring apparatus 10 may include more than one light guide 14.

In this case, only one common light source 12 is provided, and the light detector 16 is provided for each light guide 14. For example, as shown in FIG. 15, when two optical fibers which are the light guides 14 are provided, two light detectors 16: a first light detector 161 and a second light detector 162 are provided. The measurement light from the light source 12 is divided into two parts by an unshown optical branch, so that one of the divided measurement light enters the optical branch 20 connected to one of the optical fibers and the first light detector 161, whereas the other of the divided measurement light enters the optical branch 20 connected to the other of the optical fibers and the second light detector 162.

As above, the independent light detector 16 is provided for each of the light guides 14, so that it is possible to detect at more positions.

Alternatively, as shown in FIG. 16, the light guide 14 which the measurement light enters and the light guides 14 from which detected light exits may be separately configured. In this case, the measurement light from the light source 12 is directly supplied to the entrance-side light guide 14, exit light from this entrance-side light guide 14 is reflected in two directions by a mirror 30, and each reflected light is collected by a lens 32 and enters each exit-side light guide 14. Detected lights exiting from these exit-side light guides 14 enter the corresponding light detector 161 or 162.

In this configuration, branching (the optical branch 20) between the light source 12 and the light detector 16 is eliminated, and efficiency of light usage is therefore high.

Instead of the mirror 30 and the lens 32, a connecting optical fiber having an optical branching function may be used.

Although two light guides 14 in FIG. 15 and two exit-side light guides 14 in FIG. 16 are shown in the cases described by way of example, it will be appreciated that light guides can be increased to a greater number. Depending on the number, it is possible to detect at more positions.

Although the gratings 26 are produced in the order in which the wave number $k_G$ does not increase from the side close to the light source 12 to the far side on the assumption that two optical fibers are one optical fiber in FIG. 15 and FIG. 16, the gratings 26 may be produced in this order for each optical fiber. The reason is that the light detector 16 is independently provided for each optical fiber. Therefore, in FIG. 15 and FIG. 16, the sensing part 18-1 and the sensing part 18-2 may have the gratings 26 of the same wave number $k_G$.

Fifth Embodiment

The optical bending measuring apparatus 10 of the present invention can be mounted on a tubular apparatus.

For example, FIG. 17 shows an endoscope system in which the light guide 14 of the optical bending measuring apparatus 10 according to the first embodiment is disposed along an insertion section 34 of an endoscope as a tubular apparatus. This endoscope system includes the endoscope provided with the elongated insertion section 34 which is the tubular apparatus to be inserted into a subject (e.g. a body cavity (lumen)) that is an observation target, an operation section 36 coupled to the proximal end of the insertion section 34, and a connection cable 38. The endoscope system further includes a controller 40 which controls the endoscope.

Here, the insertion section 34 has, from the distal-end side to the proximal-end side of the insertion section 34, a distal-end rigid portion, an operation bending portion which bends, and a flexible tubular portion. The distal-end rigid portion is the distal end of the insertion section 34, and is a rigid material. This distal-end rigid portion is provided with an unshown imaging device.

The operation bending portion bends in desired directions in response to an operation by an endoscope operator (a worker such as doctors) of a bending operation knob provided in the operation section 36. The operator bends the operation bending portion by operating the bending operation knob. The position and direction of the distal-end rigid portion are changed by the bending of this operation bending portion, and the observation target is caught in an observation field of view which is an imaging range of the imaging device. Illumination light is applied to the observation target that has been caught as above, from an unshown illumination window provided in the distal-end rigid portion, and the observation target is illuminated. The operation bending portion includes unshown node rings that are joined along the longitudinal direction of the insertion section 34. The node rings rotate relative to one another, and the operation bending portion bends accordingly.

The flexible tubular portion has desired flexibility, and is bent by external force. The flexible tubular portion is a tubular member extending from the operation section 36.

The connection cable 38 connects the operation section 36 and the controller 40 to each other.

The controller 40 subjects an observation image obtained by the imaging device of the endoscope to image processing, and displays the image-processed observation image on an unshown display device. In the present embodiment, as shown in FIG. 17, the light source 12, the light detector 16, and the optical branch 20 of the optical bending measuring apparatus 10 are incorporated in this controller 40, and the optical fiber which is the light guide 14 is disposed to extend along the longitudinal axis direction of the insertion section 34 from this controller 40 through connection cable 38 and the operation section 36. The anti-reflector 22 is provided in the distal-end rigid portion of the insertion section 34. In this case, the sensing parts 18 are provided at corresponding positions in the optical fiber and in the operation bending portion and the flexible tubular portion of the insertion section 34.

As described above, the light detector 16 can independently measure the bending direction and bending amount (curvature) of each part of the optical fiber. Therefore, if a large number of sensing parts 18 enough for the degree of deformation of the operation bending portion and the flexible tubular portion of the insertion section 34 which are measurement targets are formed, it is possible to measure the bending amount and bending direction of the insertion section 34.

The controller 40 further includes a control and computing circuit 42. This control and computing circuit 42 controls the light emission of the light source 12. Moreover, the control and computing circuit 42 can compute a three-dimensional shape of the insertion section 34 from the bending amount and bending direction of the optical fiber, that is, the insertion section 34 measured by the light detector 16, and display the obtained three-dimensional shape on the unshown display device.

The tubular apparatus is not limited to this endoscope, and may be, for example, various probes, catheters, or over sheaths (tubes used to assist the insertion of endoscopes and catheters).

While the present invention has been described above on the basis of the embodiments, it should be understood that the present invention is not limited to the embodiments described above, and various modifications and applications can be made within the scope of the spirit of the present invention.

For example, more than one sensing part 18 are configured in the above explanation, but one sensing part 18 is also possible.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:
1. A bending detecting system comprising:
a light guide, having elongated shape, configured to guide an incident light in a propagating direction, wherein the light guide comprises:
a core; and
a cladding disposed around the core;
a first grating disposed in an adjacent area that is adjacent to the core and without contacting the core,
wherein the first grating comprises a first periodic structure along the propagating direction with a first pitch, and
wherein the first grating is configured to generate a first diffracted light from the incident light; and
a light detector configured to:
detect the first diffracted light from the first grating; and
detect bending of the light guide based upon an optical feature amount of the first diffracted light.
2. The bending detecting system according to claim 1,
wherein the light detector is configured to detect bending of the light guide based on the optical feature amount of the light guide in a surrounding area of the first grating.
3. The bending detecting system according to claim 1,
wherein the optical feature amount is at least one of an intensity of the first diffracted light detected and a center wavelength of the first diffracted light detected.
4. The bending detecting system according to claim 1, further comprising one or more processors comprising hardware,
wherein the one or more processors are configured to calculate a bending amount of the light guide in a surrounding area of the first grating based on a change of the optical feature amount.
5. The bending detecting system according to claim 4,
wherein the optical feature amount is a change of an intensity of the first diffracted light detected, the change of the intensity being caused by a change of an incident angle of the incident light into the first grating, and
wherein the one or more processors are configured to calculate the bending amount based on the change of the intensity of the first diffracted light detected.
6. The bending detecting system according to claim 1,
wherein the adjacent area is located within one wavelength of the incident light from an outer surface of the core.

7. The bending detecting system according to claim 1,
wherein the first grating is disposed in at least one of:
the cladding; and
a light transmitting material, and
wherein a refraction index of the light transmitting material is lower than a refraction index of the core.

8. The bending detecting system according to claim 4, further comprising a second grating wherein the second grating comprises a second periodic structure along the propagating direction, and the second grating has a second pitch different from the first pitch
wherein the second grating is disposed in the adjacent area that is adjacent to the core and without contacting the core, and the second grating is further configured to generate a second diffracted light from the incident light,
wherein the second grating is configured to be disposed in a second position different from a first position of the first grating about at least one of a propagating direction and a predetermined axis direction of the light guide, the predetermined axis direction being perpendicular to the propagating direction,
wherein the light detector is further configured to detect a second diffracted light output from the second grating, and
wherein the one or more processors respectively calculate each of bending amounts of a light guide in a vicinity of the first grating and the second grating along the propagating direction based on:
wavelengths of the first and second diffracted light; and
changes of the optical feature amount in the first and second diffracted light.

9. The bending detecting system according to claim 8,
wherein the second grating is configured to be disposed in a position different from the position of the first grating about the propagating direction, and
wherein the one or more processors are configured to determine a bending shape of an area which is included in the light guide and in the vicinity of the first grating and the second grating based on the bending amounts of the first grating and the second grating.

10. The bending detecting system according to claim 8,
wherein the second grating is configured to be disposed in a position different from the position of the first grating in the predetermined axis direction, and
wherein the one or more processors are configured to determine a bending direction of an area in the vicinity of the first grating and the second grating based on the bending amounts of the first grating and the second grating.

11. The bending detecting system according to claim 4, further comprising a plurality of gratings,
wherein the plurality of gratings are disposed in the adjacent area that is adjacent to the core and without contacting the core, and the plurality of gratings are further configured to generate a plurality of diffracted lights from the incident light,
wherein the plurality of gratings are configured to be disposed in different positions to each other about at least one of a propagating direction and a predetermined axis direction of the light guide, the predetermined axis direction being perpendicular to the propagating direction,
wherein the light detector is further configured to detect the plurality of diffracted lights output from the plurality of gratings, and
wherein the one or more processors respectively calculate each of bending amounts of the plurality of gratings along the propagating axis based on:
each of wavelengths of the plurality of diffracted lights; and
each of changes of the optical feature amounts in the plurality of diffracted lights.

12. The bending detecting system according to claim 4, further comprising:
a light source configured to emit the incident light;
an optical coupler configured to optically connect to the light guide and the light detector so as to allow at least part of the first diffracted light to enter the light detector; and
an anti-reflector attached to at least one end of the optical coupler and the light guide,
wherein the light detector is configured to detect a second light including the first diffracted light and the second diffracted light which is reflected by the first grating, and
wherein the one or more processors are configured to divide the first diffracted light and the second diffracted light from the detected second light.

13. A light guide body comprising:
a light guide, having elongated shape, configured to guide an incident light in a propagating direction, wherein the light guide comprises:
a core; and
a cladding disposed around the core;
a first grating disposed in an adjacent area that is adjacent to the core and without contacting the core,
wherein the first grating comprises a first periodic structure along the propagating direction with a first pitch, and
wherein the first grating is configured to generate a first diffracted light from the incident light; and
a second grating, disposed in the adjacent area,
wherein the second grating comprises a second periodic structure along the propagating direction with a second pitch, and
wherein the second grating is configured to generate a second diffracted light from the incident light,
wherein the first grating and the second grating are disposed in different predetermined axis directions of the light guide, the different predetermined axis directions being perpendicular to the propagating direction.

14. The light guide body according to claim 13,
wherein the second pitch is different from the first pitch or substantially same as the first pitch.

15. A tubular apparatus comprising the light guide body according to the claim 13.

16. A light detecting apparatus for detecting bending of a light guide, having elongated shape, configured to guide an incident light in a propagating direction, wherein the light guide comprises: a core; a cladding disposed around the core; and a grating disposed in an adjacent area that is adjacent to a portion of the circumference of the core and without contacting the core,
wherein the light detecting apparatus comprises:
a light detector configured to:
detect a diffracted light from the light guide, the diffracted light being generated by the grating from an incident light emitted into the light guide; and
detect a bending of the light guide based upon an optical feature amount of the diffracted light;

a memory configured to store alignment information indicating the portion of the circumference of the core in which the grating is disposed;

one or more processors configured to:
calculate a bending amount of the light guide in the vicinity of the grating which generates the diffracted light based on a change of the optical feature mount; and
calculate a bending direction of the light guide in the vicinity of the grating based on the alignment information.

17. The light detecting apparatus according to claim 16, wherein the optical feature amount is at least one of an intensity of the detected first diffracted light and a center wavelength of the detected first diffracted light.

18. The light detecting apparatus according to claim 16, wherein the one or more processors are configured to calculate the bending amount of the light guide in the vicinity of the first grating based on both:
wavelength of the first diffracted light; and
intensity change of the first diffracted light or shift of a center wavelength of the first diffracted light.

19. The light detecting apparatus according to claim 16, wherein the one or more processors are configured to:
determine at least a part of a three-dimensional shape of the light guide based on the bending direction and the bending amount of the light guide in the vicinity of the first grating calculated; and
control a display to display the at least the part of the three-dimensional shape of the light guide.

20. The light detecting apparatus according to claim 16, wherein the memory is configured to store information of an intensity of the first diffracted light when the light guide is substantially straight, and
wherein the one or more processors are configured to calculate the bending amount of the light guide in the vicinity of the first grating based on a difference between:
an intensity of the detected first diffracted light; and
an intensity of the first diffracted light stored in the memory.

21. A light detecting method for detecting bending of a light guide, having elongated shape, configured to guide an incident light in a propagating direction, wherein the light guide comprises: a core; a cladding disposed around the core; and a first grating disposed in an adjacent area that is adjacent to a portion of the circumference of the core and without contacting the core,
wherein the light detecting method comprises:
detecting a diffracted light from a light guide, the diffracted light being generated by the grating from an incident light emitted into the light guide;
detecting a bending of the light guide based upon an optical feature amount of the diffracted light;
access a memory configured to store alignment information indicating the portion of the circumference of the core in which the grating is disposed;
calculating a bending amount of the light guide in the vicinity of the grating which generates the diffracted light based on a change of the optical feature mount; and
calculating a bending direction of the light guide in the vicinity of the grating based on the alignment information.

22. An optical bending measuring apparatus for measuring bending of a light guide, the optical bending measuring apparatus comprising:
a light source which supplies measurement light;
a light guide which has a core and a cladding and which transmits the measurement light in a longitudinal axis direction thereof;
sensing parts provided in positions different in the longitudinal axis direction of the light guide and each having a grating, the grating being provided outside the core, and the grating generating diffracted lights from the measurement light being traveled in the core;
a light detector which detects lights including the diffracted lights output from the light guide; and
a processor which separates the diffracted lights at respective wavelengths from the lights, and independently measures bending amounts of the positions of the light guide on the basis of an intensity change of the separated diffracted lights,
wherein each of at least one part of the sensing parts in a first group is disposed in a predetermined first angle of an axial direction of the of the light guide,
wherein each of at least other part of the sensing parts in a second group is disposed in a predetermined second angle of the axial direction of the of the light guide, the predetermined second angle is different from the predetermined first angle, and
wherein at least one of period of the sensing parts in the first group is different from at least one of period of the sensing parts in the second group.

23. The optical bending measuring apparatus according to claim 22,
wherein each period of the sensing parts in the first group is different from each period of the sensing parts in the second group.

* * * * *